United States Patent

Lorenz et al.

[11] 4,035,382
[45] July 12, 1977

[54] O-ALKYL-O-[5-METHYL-7-HALO-BENZISOXAZOL(3)YL]-THIONO-(THIOL)-PHOSPHORIC (PHOSPHONIC) ACID ESTERS AND ESTER AMIDES

[75] Inventors: Walter Lorenz, Wuppertal; Ingeborg Hammann, Cologne; Wilhelm Stendel, Wuppertal, all of Germany

[73] Assignee: Bayer Aktiengesellschaft, Leverkusen, Germany

[21] Appl. No.: 487,337

[22] Filed: July 10, 1974

[30] Foreign Application Priority Data

July 19, 1973 Germany .......................... 2336720

[51] Int. Cl.² .................................... C07D 261/20
[52] U.S. Cl. ........................ 260/307 DA; 424/200
[58] Field of Search ............................ 260/307 DA

[56] References Cited

U.S. PATENT DOCUMENTS

| 3,232,951 | 2/1966 | Lorenz | 260/304 |
| 3,914,243 | 10/1975 | Lorenz et al. | 260/307 D |

FOREIGN PATENT DOCUMENTS

| 2,040,410 | 2/1972 | Germany |

*Primary Examiner*—Raymond V. Rush
*Attorney, Agent, or Firm*—Burgess, Dinklage & Sprung

[57] ABSTRACT

0-Alkyl-O-[5-methyl-7-halo-benzisoxazol-(3)yl]-thiono-(thiol)-phosphoric (phosphonic) acid esters and ester amides of the formula

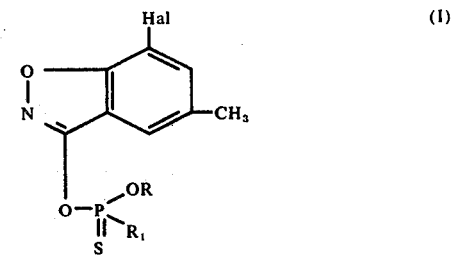

in which
R is alkyl of 1 to 6 carbon atoms,
$R_1$ is alkyl, alkoxy, alkylmercapto or alkylamino each of 1 to 6 carbon atoms, or phenyl, and
Hal is halogen,
which possess insecticidal and acaricidal properties.

7 Claims, No Drawings

O-ALKYL-O-[5-METHYL-7-HALO-BENZISOXAZOL(3)YL]-THIONO-(THIOL)-PHOSPHORIC (PHOSPHONIC) ACID ESTERS AND ESTER AMIDES

The present invention relates to and has for its objects the provision of particular new O-alkyl-O-[5-methyl-7-halo-benzisoxazol(3)yl]-thiono-(thiol)-phosphoric (phosphonic) acid esters and ester amides, which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DOS 2,040,410 that methyl-substituted benzisoxazolo-thiono-phosphoric acid esters and -phosphonic acid esters, for example O,O-diethyl-O-[5-methylbenzisoxazol-(3)-yl]-thionophosphoric acid ester (Compound A) or O-ethyl-O-[5-methyl-benzisoxazol-(3)-yl]-ethanethionophosphonic acid ester (Compound B), exhibit insecticidal and acaricidal activity.

The present invention provides benzisoxazolo-thiono-(thiol)-phosphoric(phosphonic) acid esters and esteramides of the general formula (I)

in which
R is alkyl or 1 to 6 carbon atoms,
$R_1$ is alkyl, alkoxy, alkylmercapto or alkylamino each of 1 to 6 carbon atoms, or phenyl, and
Hal is halogen.

Preferably, R is lower alkyl of 1 to 4 carbon atoms, $R_1$ is straight or branched lower alkyl, alkoxy, alkylmercapto or monoalkylamino each of 1 to 4 carbon atoms, and Hal is chlorine, bromine or iodine.

Surprisingly, the benzisoxazolo-thiono-(thiol)-phosphoric(phosphonic) acid esters and ester-amides according to the invention display substantially better insecticidal, including soil-insecticidal and acaricidal, activity than the known methyl-substituted benzisoxazolo-thiono-phosphoric acid esters of analogous structure and of the same type of action. The products according to the present invention are also employed successfully in the veterinary medicine field against animal pests (ectoparasites) such as parasitic fly larvae. The compounds according to the invention thus represent a genuine enrichment of the art.

The invention also provides a process for the preparation of a benzisoxazolo-thiono-(thiol)-phosphoric(phosphonic) acid ester or ester-amide of the formula (I) in which a 3-hydroxy-benzisoxazole of the general formula (II)

is reacted, in the presence of an acid acceptor or in the form of an alkali metal, alkaline earth metal or ammonium salt, with a thiono(thiol)-phosphoric(phosphonic) acid ester halide or ester-amide halide of the general formula (III)

in which formulae
Hal, R and $R_1$ have the above-mentioned meanings and
$Hal_1$ is halogen, preferably chlorine.

If O,O-diethylthionophosphoric acid ester chloride and 3-hydroxy-5-methyl-7-chloro-benzisoxazole are used as starting compounds, the course of the reaction can be represented by the formula scheme:

(IIIa)  (IIa)

(IV)

acid-binding agent
−HCl (I)

The following are examples of the benzisoxazole derivatives (II) and thiono-(thiol)-phosphoric(phosphonic) acid ester halides and ester-amide halides (III) which can be used as reactants:

7-chloro-, -bromo- and -iodo-5-methyl-3-hydroxy-benzisoxazole, and O,O-dimethyl-, O,O-diethyl-, O,O-dipropyl-, O,O-di-iso-propyl-, O-methyl-O-ethyl-, O-methyl-O-iso-propyl-, O-ethyl-O-iso-propyl-, O-methyl-O-butyl-, O,O-dibutyl-, O,O-di-iso-butyl- and O-tert.-butyl-O-methyl-thionophosphoric acid ester chloride, as well as O-methyl-methane-, O-ethyl-propane-, O-iso-propyl-ethane-, O-butyl-methane-, O-methyl-iso-propane-, O-methyl-ethane-, O-ethyl-ethane-, O-propyl-methane, O-butyl-ethane-, O-methyl-phenyl-, O-ethyl-phenyl- and O-n-propyl-phenyl-thionophosphonic acid ester chloride, as well as O,S-dimethyl-, O,S-diethyl-, O,S-di-n-propyl-, O,S-di-iso-propyl-, O,S-di-n-butyl-, O-methyl-S-ethyl-, O-ethyl-S- n-propyl-, O-ethyl-S-iso-propyl- and O-n-propyl-S-n-butylthionothiolphosphonic acid ester chloride, and also O-methyl-N-methyl-, O-methyl-N-ethyl, O-methyl-N-n-propyl-, O-methyl-N-iso-propyl-, O-methyl-N-n-butyl-, O-ethyl-N-ethyl-, O-n-propyl-N-ethyl- and O-n-propyl-N-n-propylthionophosphoric acid ester-amide chloride.

The thiono(thiol)-phosphoric(phosphonic) acid ester halides and ester-amide halides (III) required as reactants are known and can be prepared according to customary processes, as can the 3-hydroxy-benzisoxazoles (II), as described in Chem. Ber. 100, 954—960 [1967].

The reaction according to the invention is preferably carried out in the presence of a solvent, which term includes a mere diluent. Practically all inert organic solvents can be used for this purpose. These in particular include aliphatic and aromatic optionally chlorinated hydrocarbons, such as benzene, toluene, xylene, benzine, methylene chloride, chloroform, carbon tetrachloride and chlorobenzene; ethers, such as diethyl ether, dibutyl ether and dioxane; ketones, such as acetone, methyl ethyl ketone, methyl iso-propyl ketone and methyl iso-butyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and potassium methylate and sodium ethylate and potassium ethylate, and also aliphatic, aromatic or heterocyclic amines, for example triethylamine, trimethylamine, dimethylaniline, dimethylbenzylamine and pyridine, have proved particularly suitable.

The reaction temperature can be varied within a wide range. In general, the reaction is carried out at about 0° to 120° C, preferably about 40° to 70° C. The reaction is generally carried out under normal pressure.

To carry out the process, the benzisoxazole component is in most cases employed in 10–20% excess. The reaction is preferably carried out in the presence of one of the abovementioned solvents and in the presence of an acid acceptor, at the indicated temperatures, and after stirring for several hours — with warming, if necessary — the reaction mixture may be worked up in the usual manner.

Most of the compounds according to the invention are obtained in the form of colorless and colored oils which cannot be distilled without decomposition but can be freed of the last volatile constituents by so-called "slight distillation", that is to say prolonged heating under reduced pressure to moderately elevated temperatures, and they can be purified in this way. They are characterized especially by the refractive index. Some of the compounds may be obtained in crystalline form with a sharp melting point.

As has already been mentioned, the new benzisoxazolo-thiono(thiol)-phosphoric(phosphonic) acid esters and ester-amides are distinguished by an outstanding insecticidal and acaricidal activity. They possess a good action against both sucking and biting insects and also against mites (Acarinae). They may be employed successfully in the veterinary medicine field against animal pests (ectoparasites), such as parasitic fly larvae. At the same time, they display a low phytotoxicity and some soil-insecticidal properties are also displayed.

For these reasons, the compounds according to the invention are used as pesticides in plant protection and protection of stored products, and also in the hygiene field and veterinary field.

To the sucking insects there belong, in the main, aphids (Aphidae) such as the green peach aphid (*Myzus persicae*), and bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularis*), the assassin bug (*Rhodnius prolixus*) and Chagas' bug (*Triatoma infestans*) and, further cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterannean flour moth (*Ephestia kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*), and the saw-toothed grain beetle (*Oryzaephilus surinamensis*), and also species living in the soil, for example wireworms (*Agriotes* spec.) and larvae of the cockchafer (*Melolontha melolontha*); cockroachs, such as the German cockroach (*Blattella germanica*), American cockroach (*Periplaneta americana*), Madeira cockroach (*Leucophaea* or *Rhyparobia maderae*), oriental cockroach (*Blatta orientalis*), and giant cockroach (*Blaberus giganteus*) and the black giant cockroach (*blaberus fuscus*) as well as *Henschoutedenia flexivitta*; further, *Orthoptera*, for example the house cricket (*Gryllus domesticus*); termites such as the eastern subterranean termite (*Reticuitermes flavipes*) and *Hymenoptera* such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*) the little house fly (*Fannia canicularis*), the black blow fly (*Phormia regina*) and bluebottle fly (*Cal-*

*liphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acari*) there are classed, in particular, the spider mites (*Tetranychidae*) such as the two-spotted spider mite (*Tetranychus telarius* = *tetranychus althaeae* or Tetranychus urticae) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant comparable or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticides surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersable inert finely divided carrier solid, and/or (2) a dispersable carrier liquid such as an inert organic solvent and/or water peferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compound can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only upon to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae were killed whereas 0% means that none of the beetle larvae were killed.

The active compounds, the concentrations of the active compounds, the evaluation times and the results can be seen from Table 1.

Table 1

| (Phaedon larvae test) Active compound | Active compound concentration in % by weight | Degree of destruction in % after 3 days |
|---|---|---|
| (known) (A) | 0.1 0.01 0.001 | 100 100 20 |
| (known) (B) | 0.1 0.01 0.001 | 100 100 0 |
| (7) | 0.1 0.01 0.001 | 100 100 85 |

Table 1-continued

| (Phaedon larvae test) Active compound | Active compound concentration in % by weight | Degree of destruction in % after 3 days |
|---|---|---|
| (1) | 0.1 0.01 0.001 0.0001 | 100 100 100 30 |
| (8) | 0.1 0.01 0.001 | 100 100 90 |
| (3) | 0.1 0.01 0.001 | 100 100 100 |
| (9) | 0.1 0.01 0.001 | 100 100 85 |
| (18) | 0.1 0.01 0.001 | 100 100 100 |
| (4) | 0.1 0.01 0.001 | 100 100 80 |
| | 0.1 0.01 0.001 | 100 100 95 |

Table 1-continued (Phaedon larvae test)

| Active compound | Active compound concentration in % by weight | Degree of destruction in % after 3 days |
|---|---|---|
| (14) Br-C₆H₂(CH₃)-isoxazole-C(=NO)-S-P(=O)(OCH₃)(OC₃H₇i) | 0.1<br>0.01<br>0.001 | 100<br>100<br>90 |
| (13) Br-C₆H₂(CH₃)-isoxazole-C(=NO)-S-P(=O)(OC₂H₅)(OC₃H₇) (15) | 0.1<br>0.01<br>0.001 | 100<br>100<br>90 |

EXAMPLE 2

Lucilia grub test

Solvent: 3.5 parts by weight of alkylglycol monomethyl ether

Emulsifier: 3.5 parts by weight of nonlyphenol polyglycol ether

To prepare a suitable preparation of active compound, 3 parts by weight of active compound were mixed with the stated amount of solvent, the stated amount of emulsifier was added and the concentrate was diluted to the desired concentration with water.

About 50 young blow fly larvae (*Lucilia cuprina*) were placed on a piece of meat which was subsequently placed in a small glass. The latter already contained the aqueous preparation of the active compound.

After 48 hours, the degree of destruction in % was determined. 100% denotes that all grubs were killed. 0% denotes that no grubs whatsoever were killed.

The active compounds, active compound concentrations and results can be seen from Table 2.

EXAMPLE 3

Stable fly test (Test on adult *Stomoxys calcitrans* / dish test in vitro)

Solvent:
35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contained the abovementioned proportion of emulsifier, and the concentrate thus obtained was diluted with water to the desired concentration.

Test object: Unfed 1 day old flies (*Stomoxys calcitrans*)

Test procedure: 10 flies per concentration (stunned by means of $CO_2$) were transferred onto filter paper discs (diameter 7.5 cm) which were impregnated with active compound and which were located in Petri dishes (polystyrene). The treated discs were prepared by pipetting 1 ml of the concentrations to be tested (100 and 10 ppm) onto the discs and then transferring and storing the discs in a climatically controlled test room ($27°C \pm 1°C$, 70% relative humidity + 5%). The action was checked after 24 hours.

Test criteria: The criterion of action was the death of the treated flies (signs of death = lack of deliberate movement of the limbs after irritation with a dissecting needle). 100% denotes that all flies were killed. 0% denotes that no flies whatsoever were killed.

Table 2

(Lucilia and Stomoxys tests)

| Active compound | Parasite | Active compound concentration in ppm | Degree of destruction in % |
|---|---|---|---|
| (1) Cl-C₆H₂(CH₃)-isoxazole-C(=NO)-O-P(=S)(OC₂H₅)₂ | Lucilia cuprina | 100 | 100 |
| (2) Cl-C₆H₂(CH₃)-isoxazole-C(=NO)-O-P(=S)(OCH₃)₂ | Lucilia cuprina<br>Stomoxys calcitrans | 100<br>10<br>100<br>10 | 100<br>>50<br>100<br>100 |

Table 2-continued
(Lucilia and Stomoxys tests)

| Active compound | Parasite | Active compound concentration in ppm | Degree of destruction in % |
|---|---|---|---|
| (3) 7-Cl, 5-CH₃ benzisoxazole with O-P(=S)(OC₂H₅)(C₂H₅) | Lucilia cuprina<br>Lucilia cuprina<br>Stomoxys calcitrans | 100<br>10<br>100 | 100<br>100<br>100 |
| (4) 7-Cl, 5-CH₃ benzisoxazole with O-P(=S)(O-C₂H₅)(O-C₃H₇-i) | Lucilia cuprina | 100 | 100 |
| (5) 7-Cl, 5-CH₃ benzisoxazole with O-P(=S)(O-C₂H₅)(S-C₃H₇-n) | Lucilia cuprina | 100 | 100 |
| (7) 7-Br, 5-CH₃ benzisoxazole with S-P(=O)(OCH₃)₂ | Lucilia cuprina<br>Lucilia cuprina | 100<br>10 | 100<br>100 |
| (8) 7-Br, 5-CH₃ benzisoxazole with O-P(=S)(OC₂H₅)₂ | Lucilia cuprina | 100<br>10 | 100<br>>50 |
| (9) 7-Br, 5-CH₃ benzisoxazole with O-P(=S)(OC₂H₅)(C₂H₅) | Lucilia cuprina | 100<br>10 | 100<br>>50 |
| 7-Br, 5-CH₃ benzisoxazole with O-P(=S)(OC₃H₇-i)(OC₂H₅) | Lucilia cuprina | 100 | 100 |

Table 2-continued

| | (Lucilia and Stomoxys tests) | Active compound concentration in ppm | Degree of destruction in % |
|---|---|---|---|
| Active compound | Parasite | | |
| (10) | | | |

EXAMPLE 4

Tetranychus test (resistant)
Solvent: 3 parts by weight
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*), which had a height of approximately 10 – 30 cm, were sprayed with the preparation of the active compound until dripping wet. These bean plants were heavily infested with the common or two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from Table 3.

Table 3

(Tetranychus test)

| Active compound | Active compound concentration in % by weight | Degree of destruction in % after 2 days |
|---|---|---|
| (known) (A) | 0.1<br>0.01 | 60<br>0 |
| (known) (B) | 0.1 | 0 |
| (11) | 0.1<br>0.01 | 100<br>98 |
| 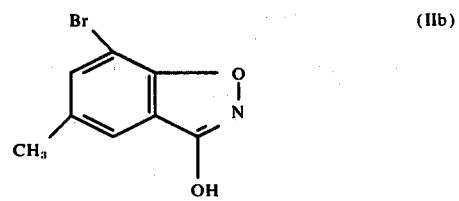 (12) | 0.1<br>0.01<br>0.001 | 100<br>90<br>45 |

EXAMPLE 5 a. The compounds (II) used as starting materials can be prepared, for example, according to Chem. Ber. 100, 954–960 (1967) as follows:

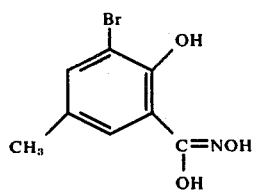 (IIb)

109 ml (1.5 moles) of thionyl chloride were added dropwise to 246 g (1 mole) of the compound of the formula in 1000 ml of toluene and 800 ml of ethyl acetate, and the reaction mixture was then brought to 25° C under reduced pressure. After one hour, a clear solution was obtained, to which 174 ml of triethylamine was added over the course of 10 minutes while stirring and cooling with solid carbon dioxide/acetone. The solution was then poured into water, concentrated sodium hydroxide solution was added until an alkaline reaction to triazene paper was obtained, the phases were separated, the mixture was acidified and the precipitate was filtered off. 173 g (76% of theory) of 3-hydroxy-5-methyl-7-bromo-benzisoxazole of melting point 235° C were thus obtained. When recrystallized from methanol, the compound had a melting point of 240° C, with decomposition.

The following compound was prepared analogously:

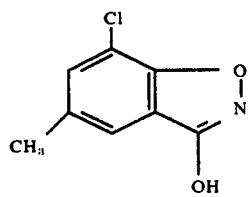
(11a)

Melting point 228° C; yield 85% of theory.

b)
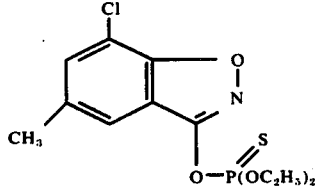
(1)

A mixture of 44 g (0.24 mole) of 3-hydroxy-5-methyl-7-chloro-benzisoxazole (melting point 228° C) in 300 ml of acetonitrile and 30 g (0.26 mole) of potassium carbonate was stirred for 30 minutes at 40 – 50° C. 38 g (0.2 mole) of O,O-diethyl-thinophosphoric acid ester chloride were then added dropwise at about 50° C. An exothermic reaction was not observed. The reaction was therefore completed by stirring for 2 hours at 50°–60° C. After cooling, the inorganic salts which had separated out were filtered off. The solvent was largely distilled from the filtrate under reduced pressure. The distillation residue was mixed with water and the oil which had separated out was taken up in toluene. The toluene solution was washed with 2 N sodium hydroxide solution and finally with water. After drying the organic layer, the toluene was distilled off. An oil remained, which rapidly crystallized on trituration with petroleum ether and standing the mixture in ice water. 55 g (82% of theory) of O,O-diethyl-O-[5-methyl-7-chloro-benzisoxazol(3)yl]-thionophosphoric acid ester were thus obtained as yellowish needles of melting point 57° C.

The following compounds were prepared analogously:

Table 4

| Compound No. | Structure | Physical properties [refractive index, melting point] |
|---|---|---|
| 2 | Cl-substituted benzisoxazole with O—P(OCH$_3$)$_2$, S | 85° C |
| 3 | Cl-substituted benzisoxazole with O—P(C$_2$H$_5$)(OC$_2$H$_5$), S | 65° C |
| 4 | Cl-substituted benzisoxazole with O—P(OC$_2$H$_5$)(OC$_3$H$_7$-i), S | $n_D^{20}$: 1.5290 |
| 5 | Cl-substituted benzisoxazole with O—P(OC$_2$H$_5$)(SC$_3$H$_7$-n), S | $n_D^{21}$: 1.5615 |
| 6 | Cl-substituted benzisoxazole with O—P(OC$_2$H$_5$)(NH—C$_2$H$_5$), S | melting point 111° C |
| 7 | Br-substituted benzisoxazole with O—P(OCH$_3$)$_2$, S | melting point 93° C |
| 8 | Br-substituted benzisoxazole with O—P(OC$_2$H$_5$)$_2$, S | melting point 54° C |
| 9 | Br-substituted benzisoxazole with O—P(OC$_2$H$_5$)(C$_2$H$_5$), S | melting point 79° C |
| 10 | Br-substituted benzisoxazole with O—P(OC$_2$H$_5$)(OC$_3$H$_7$-i), S | $n_D^{21}$: 1.5415 |

Table 4-continued

| Compound No. | Structure | Physical properties [refractive index, melting point] |
|---|---|---|
| 11 | 7-Cl, 5-methyl-benzisoxazol-3-yl O-P(=S)(CH₃)(OC₃H₇-i) | melting point 78° C |
| 12 | 7-Br, 5-methyl-benzisoxazol-3-yl O-P(=S)(CH₃)(OC₃H₇-i) | melting point 67° C |
| 13 | 7-Br, 5-methyl-benzisoxazol-3-yl O-P(=S)(OCH₃)(OC₃H₇-i) | $n_D^{\;}$: 1.5505 |
| 14 | 7-Br, 5-methyl-benzisoxazol-3-yl O-P(=S)(OCH₃)(OC₃H₇-n) | $n_D^{\;}$: 1.5516 |
| 15 | 7-Br, 5-methyl-benzisoxazol-3-yl O-P(=S)(OC₂H₅)(OC₃H₇-n) | $n_D^{\;}$: 1.5393 |
| 16 | 7-Br, 5-methyl-benzisoxazol-3-yl O-P(=S)(C₆H₅)(OC₂H₅) | melting point 72° C |
| 17 | 7-Cl, 5-methyl-benzisoxazol-3-yl O-P(=S)(OCH₃)(OC₃H₇-i) | $n_D^{\;}$: 1.5368 |
| 18 | 7-Cl, 5-methyl-benzisoxazol-3-yl O-P(=S)(OCH₃)(OC₃H₇-n) | $n_D^{\;}$: 1.5375 |
| 19 | 7-Cl, 5-methyl-benzisoxazol-3-yl O-P(=S)(OC₂H₅)(OC₃H₇-n) | $n_D^{\;}$: 1.5285 |
| 20 | 7-Cl, 5-methyl-benzisoxazol-3-yl O-P(=S)(C₆H₅)(OC₂H₅) | $n_D^{\;}$: 1.5915 |

The compounds (II) used as starting materials can be prepared, for example, according to Chem. Ber. 100, 954–960 (1967) as follows:

Other compounds which can be similarly prepared include:

O,O-di-n-butyl-O-[5-methyl-7-iodo-benzisoxazol-(3)yl]-thionophosphoric acid ester.

It will be appreciated that the instant specification and examples are set forth by way of illustration and not limitation, and that various modifications and changes may be made without departing from the spirit and scope of the present invention.

What is claimed is:

1. An O-alkyl-O-[5-methyl-7-halo-benzisoxazol-(3)yl]-thiono-(thiol)-phosphoric(phosphonic) acid ester or ester-amide of the formula

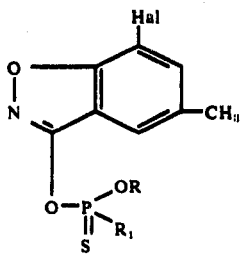

in which
- R is alkyl of 1 to 6 carbon atoms,
- R₁ is alkyl, alkoxy, alkylmercapto or alkylamino each of 1 to 6 carbon atoms, or phenyl, and
- Hal is halogen.

2. A compound according to claim 1 in which R is alkyl of 1 to 4 carbon atoms, R₁ is straight or branched alkyl, alkoxy, alkylmercapto or mono-alkylamino each of 1 to 4 carbon atoms, and Hal is chlorine, bromine or iodine.

3. The compound according to claim 1 wherein such compound is O,O-diethyl-O-[5-methyl-7-chlorobenzisoxazol(3)yl]-thionophosphoric acid ester of the formula

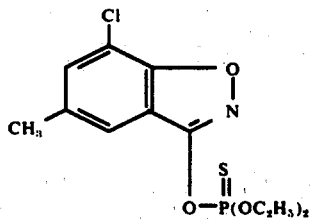

4. The compound according to claim 1 wherein such compound is O-ethyl-S-n-propyl-O-[5-methyl-7-chloro-benzisoxazol(3)yl]-thionothiolphosphoric acid ester of the formula

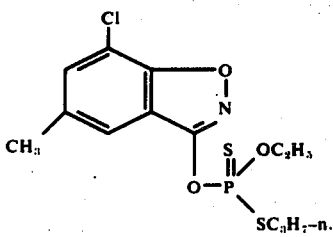

5. The compound according to claim 1 wherein such compound is O-isopropyl-O-[5-methyl-7-chlorobenzisoxazol(3)yl]-methanethionophosphonic acid ester of the formula

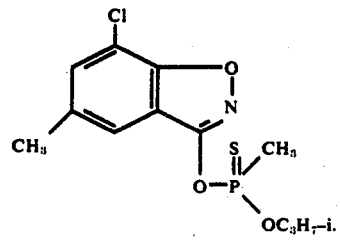

6. The compound according to claim 1 wherein such compound is O-isopropyl-O-[5-methyl-7-bromo-benzisoxazol(3)yl]-methanethionophosphonic acid ester of the formula

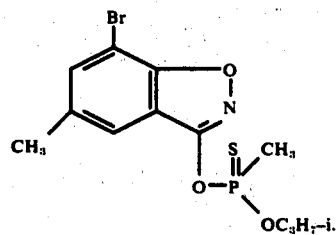

7. The compound according to claim 1 wherein such compound is O-ethyl-O-n-propyl-O-[5-methyl-7-bromobenzisoxazol(3)yl]-thionophosphoric acid ester of the formula

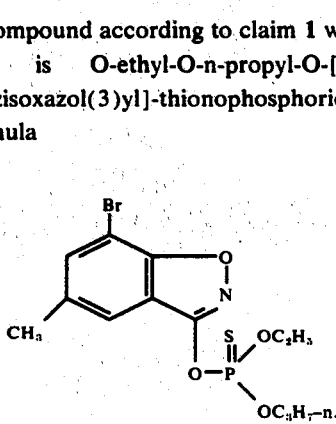

* * * * *